United States Patent
Vigliante

(10) Patent No.: US 9,541,511 B2
(45) Date of Patent: Jan. 10, 2017

(54) XRF MEASUREMENT APPARATUS FOR DETECTING CONTAMINATIONS ON THE BEVEL OF A WAFER

(71) Applicant: Bruker AXS GmbH, Karlsruhe (DE)

(72) Inventor: Assunta Vigliante, Stuttgart (DE)

(73) Assignee: Bruker AXS GmbH, Karlsruhe (DE)

( * ) Notice: Subject to any disclaimer, the term of this patent is extended or adjusted under 35 U.S.C. 154(b) by 226 days.

(21) Appl. No.: 14/159,469

(22) Filed: Jan. 21, 2014

(65) Prior Publication Data

US 2014/0211914 A1 Jul. 31, 2014

(30) Foreign Application Priority Data

Jan. 30, 2013 (EP) .................................... 13153344

(51) Int. Cl.
*G01N 23/223* (2006.01)
*G01N 21/95* (2006.01)
*G01N 23/20* (2006.01)

(52) U.S. Cl.
CPC ........ *G01N 23/223* (2013.01); *G01N 21/9501* (2013.01); *G01N 21/9503* (2013.01); *G01N 23/20025* (2013.01); *G01N 2223/076* (2013.01); *G01N 2223/6116* (2013.01); *G01N 2223/652* (2013.01)

(58) Field of Classification Search
None
See application file for complete search history.

(56) References Cited

U.S. PATENT DOCUMENTS

| 4,599,741 A | * | 7/1986 | Wittry | G01N 23/223 378/45 |
| 5,220,591 A | * | 6/1993 | Ohsugi | G01N 23/2206 378/44 |
| 5,430,786 A | * | 7/1995 | Komatsu | G01N 23/223 378/45 |

(Continued)

FOREIGN PATENT DOCUMENTS

| JP | 09283601 A | * 10/1997 | ............. H01L 21/68 |
| JP | 2002005858 | 1/2002 | |
| JP | 2009133658 | 6/2009 | |

OTHER PUBLICATIONS

Kohno et al., "Detection of Metal Contamination on Silicon Wafer Backside and edge by New TXRF methods", AIP Conference Proceedings 1173, 67 (2009).*

(Continued)

*Primary Examiner* — Michael Logie
(74) *Attorney, Agent, or Firm* — Paul Vincent

(57) ABSTRACT

An XRF (XRF=x-ray fluorescence) measurement apparatus (1) has an x-ray source (2) for generating x-rays (4), x-ray optics (3) for directing x-rays (4) from the x-ray source (2) to a sample (5) and an EDS (EDS=energy dispersive spectroscopy) detector (7) for detecting fluorescent x-rays (14) from the sample (5). The apparatus is characterized in that the sample (5) is a wafer (6), in particular a Si wafer, wherein the x-ray optics (3) is positioned to direct the x-rays (4) onto the bevel (12) of the wafer (6). The x-ray source (2) plus the x-ray optics (3) has a brilliance of at least $5*10^7$ counts/sec mm$^2$, preferably at least $1*10^8$ counts/sec mm$^2$. The apparatus allows an improved contamination control of wafers, in particular silicon wafers.

15 Claims, 5 Drawing Sheets

(56) References Cited

U.S. PATENT DOCUMENTS

| | | | | |
|---|---|---|---|---|
| 5,732,120 | A * | 3/1998 | Shoji | G01N 23/223 378/210 |
| 5,778,039 | A | 7/1998 | Hossain | |
| 5,892,809 | A * | 4/1999 | Wittry | G21K 1/06 378/45 |
| 5,930,586 | A * | 7/1999 | Jain | H01L 22/12 257/E21.53 |
| 5,949,847 | A * | 9/1999 | Terada | G01N 23/221 378/86 |
| 6,677,595 | B1 * | 1/2004 | Aiba | H01J 37/20 250/440.11 |
| 6,977,986 | B1 * | 12/2005 | Beanland | G01N 23/20 378/34 |
| 7,202,476 | B2 * | 4/2007 | Suga | G01N 23/225 250/310 |
| 7,248,670 | B2 * | 7/2007 | Hoghoj | B82Y 10/00 378/145 |
| 7,919,760 | B2 * | 4/2011 | Jau | H01J 37/20 250/310 |
| 7,929,667 | B1 * | 4/2011 | Zhuang | H05G 2/005 378/119 |
| 8,008,629 | B2 * | 8/2011 | Adamec | H01J 37/1472 250/307 |
| 2003/0128809 | A1 * | 7/2003 | Umezawa | H01L 22/12 378/70 |
| 2004/0135232 | A1 * | 7/2004 | Bakel | H01L 23/544 257/620 |
| 2005/0117239 | A1 | 6/2005 | Hoghoj | |
| 2006/0083350 | A1 * | 4/2006 | Gerndt | G01T 1/2914 378/70 |
| 2006/0088139 | A1 * | 4/2006 | Nakano | G01N 23/20016 378/79 |
| 2008/0013822 | A1 * | 1/2008 | Pai | G01N 21/9501 382/145 |
| 2011/0141463 | A1 * | 6/2011 | Chikamatsu | G01N 21/956 356/237.5 |
| 2012/0294418 | A1 * | 11/2012 | Yellepeddi | G01N 23/207 378/44 |
| 2013/0048489 | A1 * | 2/2013 | Yamaguchi | C23C 14/0068 204/192.15 |
| 2015/0194287 | A1 * | 7/2015 | Yun | H01J 35/08 378/44 |
| 2015/0233845 | A1 * | 8/2015 | Fukuda | G01N 23/20016 378/44 |

OTHER PUBLICATIONS

P. Pianetta et al., "Characterization of Silicon Wafer Surfaces with SR-TXRF", The Rigaku Journal, vol. 19, No. 2 & vol. 20, No. 1, 2003.

Hidekazu Hayashi et al., "Cu Spin Cleaning Evaluation by SOR X-ray Fluorescence Analysis" Solid State Phenomena vol. 103-104, Apr. 2005, pp. 217-220.

Y. Tsusaka at al., "Hyogo beamline at SPring-8: multiple station beamline with the TROIKA concept", Nuclear Instruments and Methods in Physics Research A 467-468 (2001) pp. 670-673.

Hiroshi Kohno et al., "Detection of Metal Contamination on Silicon Wafer Backside and Edge by New TXRF Methods", AIP Conference Proceedings, vol. 1173, May 11, 2009, May 15, 2009, pp. 67-71.

Chris M. Sparks et al., "Novel Technique for Contamination Analysis around the Edge, the Bevel, and the Edge Exclusion Area of 200 and 300 mm Silicon Wafers", Proceedings of SPIE, vol. 5041, Jul. 15, 2003, Pa. 99-104.

* cited by examiner

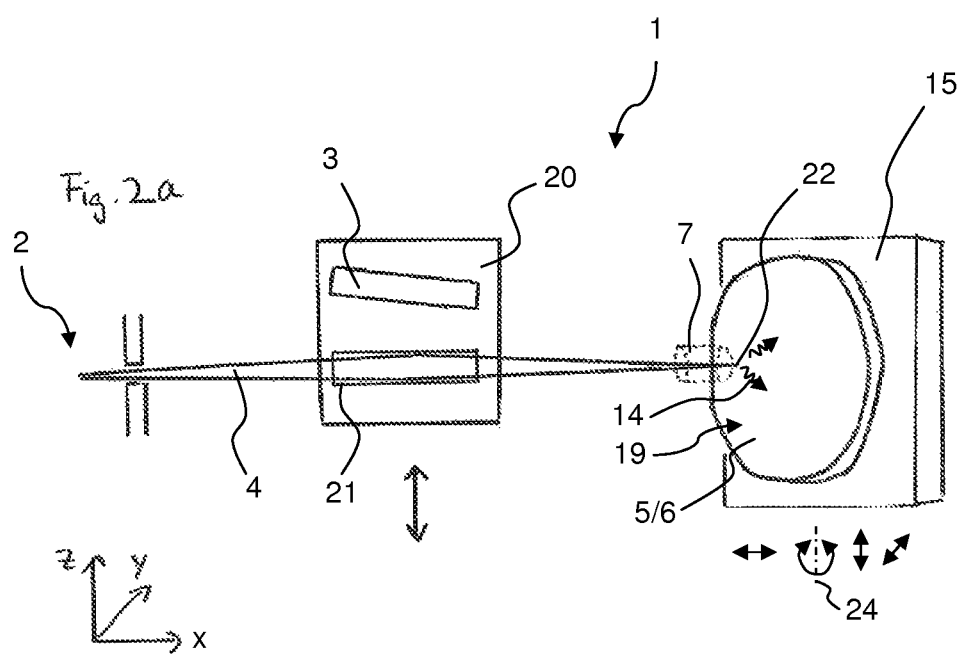

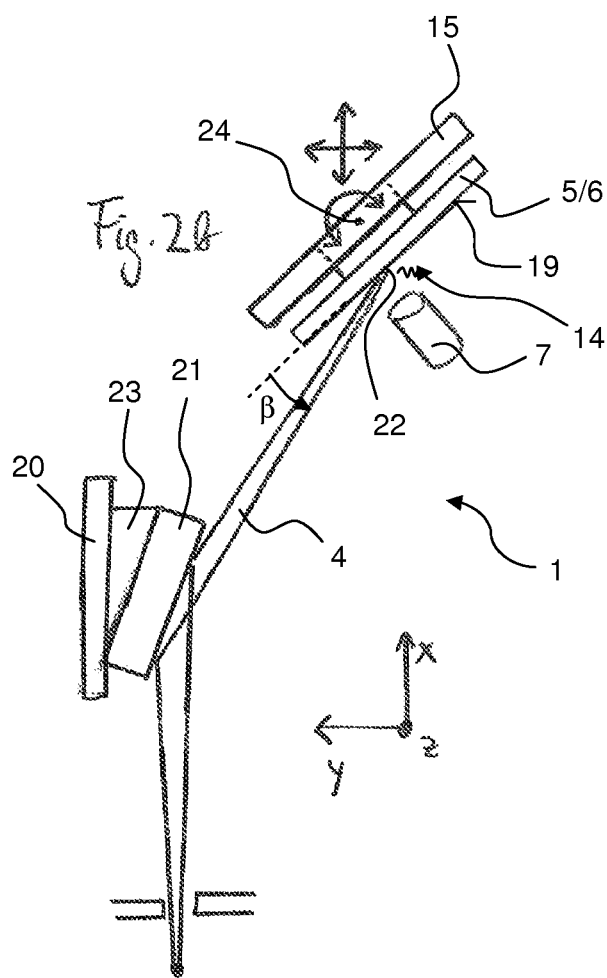

XRF MEASUREMENT APPARATUS FOR DETECTING CONTAMINATIONS ON THE BEVEL OF A WAFER

This application claims Paris convention priority from EP 13 153 344.0 filed Jan. 30, 2013, the entire disclosure of which is hereby incorporated by reference.

BACKGROUND OF THE INVENTION

The invention relates to an XRF (XRF=x-ray fluorescence) measurement apparatus, comprising
an x-ray source for generating x-rays,
x-ray optics for directing x-rays from the x-ray source to a sample,
the sample,
and an EDS (EDS=energy dispersive spectroscopy) detector for detecting fluorescent x-rays from the sample.

Such an XRF measurement apparatus is known from U.S. Pat. No. 5,778,039 A.

Wafers, in particular silicon wafers, are a basic component in the production of semiconductor electronics. These semiconductor electronics are based on pn-transitions, in particular in diodes and transistors. Semiconductor material of p-type and n-type is produced by carefully controlling the chemical composition of a basic material (such as silicon). More specifically, dopant materials having a number of valence electrons different from the basic material are deliberately added to the basic material.

However, contaminations may act similar to dopant materials, changing the properties of the semiconductor material in an unintended way. Accordingly, semiconductor production is performed under clean room conditions, and the contamination levels are monitored closely.

For silicon wafers, it has been proposed to examine the flat side surfaces of the wafer by means of TXRF (total reflection x-ray fluorescence) spectroscopy. In TXRF, a typically monochromatic x-ray beam is directed to a sample surface, and characteristic x-rays resulting from the refilling of depleted deep electron shells of the sample material are detected. Contaminations of the sample surface result in x-ray peaks at additional wavelengths, as compared to the sample material alone. XRF spectra may be evaluated quantitatively, for determining the amount of contaminations. The flat side surface may be completely scanned with the x-ray beam ("wafer mapping"), if desired.

During production processes, wafers have to be transported at numerous occasions. For this purpose, grippers typically act on the bevel of the wafer; the bevel is also sometimes called "grip edge". Thus contaminations of the flat side surfaces of the wafer shall be avoided.

However, contaminations of the bevel may be passed on to the flat surfaces later on, for example by surface diffusion, in particular at elevated temperatures. Therefore, bevel contaminations should be avoided, too, and accordingly, bevel contaminations should be monitored for this purpose.

For monitoring bevel contaminations, it is possible to wipe the edge of the wafer with a receptive carrier (such as a cotton bud), and to analyze the receptive carrier, for example with ICP-MS (inductively coupled plasma mass spectrometry). However, this is a complex and time-consuming procedure, and the receptive carrier itself may contaminate the wafer.

It is the object of the invention to allow an improved contamination control of wafers, in particular silicon wafers.

SUMMARY OF THE INVENTION

This object is achieved, in accordance with the invention, by an XRF measurement apparatus as introduced in the beginning, characterized in that the sample is a wafer, in particular a Si wafer, wherein the x-ray optics is positioned to direct the x-rays onto the bevel of the wafer, and that the x-ray source plus the x-ray optics has a brilliance of at least $5*10^7$ counts/sec mm$^2$, preferably at least $1*10^8$ counts/sec mm$^2$.

The invention proposes to use XRF on the bevel (edge) of a wafer, such as a silicon wafer, and to direct x-rays onto the bevel accordingly. Preferably, the (primary) x-ray hits only the bevel of the wafer, and not the flat side surface of the wafer when the bevel is analyzed. Further, the invention proposes to apply an x-ray source, in particular of microsource type, with a high brilliance. This ensures that a sufficient signal level is achieved from possible contaminations, so contaminations can reliably be detected. The XRF measurement can be evaluated immediately, without delays for, for example, transporting a receptive carrier to a mass spectrometer. The inventive method is non-destructive and not likely to introduce new contaminations.

Note that typical wafers used as samples, in accordance with the invention, are basically circular disc shaped, often with a cut-out part along a secant. Generally, the surface area of the flat side of a wafer is at least 10 cm$^2$, often 100 cm$^2$ or more, and the thickness is 750 µm or less, often 375 µm or less. Typical wafer materials are silicon or germanium; however other materials such as aluminum oxide or steel are also possible.

In a preferred embodiment of the inventive apparatus, the x-ray optics and the wafer are positioned such that the x-rays hit the surface of the wafer at the bevel at an angle of between 0.05° and 6°. This geometry results in larger signal levels from contaminations, as compared to incident primary beams closer to a perpendicular orientation. More contamination material can be illuminated at the same time, and total reflection may occur at the wafer's surface what keeps the signal from wafer material low.

Preferred is also an embodiment, wherein the x-ray optics and the wafer are positioned such that the x-rays directed to the sample propagate essentially in a plane parallel to a flat side of the wafer. This geometry also leads to larger signal levels from contaminations, as compared to incident primary beams closer to perpendicular orientation, for typical wafer designs, using the x-ray beam basically tangentially. Again, more contamination material can be illuminated at the same time.

Further preferred is an embodiment wherein the wafer is oriented with the surface normal of a flat side of the wafer being oriented horizontally. This saves space, and in some situations may allow a quick change of the investigated wafer by moving a row of wafers horizontally.

Also preferred is an embodiment wherein the x-rays directed to the sample propagate in an essentially horizontal direction. This offers a good access to the equipment and samples in practice.

In an advantageous embodiment, the x-ray source is of metal jet target type. Metal jet target type x-ray sources allow a particularly high brilliance. Heat in the target material is easily dissipated;
further, the target area hit by an electron beam can be chosen small, according to the diameter of the jet. Note that source spot diameters of 100 µm or less (qualifying as micro-source) are preferred, in accordance with the invention.

In a preferred embodiment, the x-ray optics include a Montel mirror or a Göbel mirror or a double curved multilayer mirror. These parts have shown high efficiency in focusing or collimating x-ray beams. In particular, a multilayer mirror having a single reflective surface curved with respect to both a sagittal and a meridional direction of incident x-rays (see U.S. Pat. No. 7,248,670 B2), referred to as a double curved multilayer mirror, may be used, in accordance with the invention. Note that the x-ray optics may comprise further parts, alternatively or in addition, such as capillary optics or apertures.

Particularly preferred is an embodiment wherein the bevel of the wafer is located in a focus of the x-ray optics. Then the flux of primary x-rays can be used efficiently for XRF analysis of the wafer bevel, and influences from areas away from the bevel may be excluded or at least minimized. Alternatively, a parallel x-ray beam may be used. Further alternatively or in addition, areas next to the bevel may be shadowed, for example using a mask or an aperture.

Advantageous is further an embodiment wherein at a position at the surface of the sample, the width of the x-rays directed to the sample matches the width of the wafer. This makes sure that basically all contaminations may be detected in a single revolution of the wafer, and influences from areas away from the bevel may be excluded. Further, the primary x-rays may be used efficiently. Note that the wafer typically has a thickness of 750 µm or less, such as 450 µm or 375 µm.

Particularly preferred is an embodiment providing that the apparatus further comprises an auxiliary x-ray optics for directing x-rays from the x-ray source to the sample and switching means for switching the apparatus between a first operation mode and a second operation mode,
wherein in the first operation mode, the x-ray optics are positioned to direct x-rays form the x-ray source onto the bevel of the wafer, and wherein in the second operation mode, the auxiliary x-ray optics are positioned to direct x-rays form the x-ray source onto a flat side of the wafer. Such an apparatus allows an investigation of the complete wafer surface, including the flat side surface (at least the front surface, or even both flat side surfaces of back and front) and the bevel, no contaminations can be missed then.

In a preferred further development of this embodiment, the switching means comprise a first moving stage for exchanging the x-ray optics with the auxiliary x-ray optics in the path of the x-rays. The first moving stage is typically motorized and allows a quick and simple change of the x-ray optics.

Another preferred further development provides that the switching means comprise a second moving stage for pivoting and/or shifting the wafer relative to the path of the x-rays. The second moving stage is typically motorized and simplifies the change of the area of the sample illuminated with the primary x-ray beam.

A preferred embodiment is characterized in that the apparatus further comprises
  a further EDS detector for detecting fluorescent x-rays from the sample, and
  a handling stage for shifting the wafer relative to the path of the x-rays directed to the sample in two independent, in particular orthogonal, directions transverse to the x-rays directed to the sample, and for rotating the wafer with respect to a rotation axis perpendicular to a flat side of the wafer,
in particular wherein the EDS detector and the further EDS detector view the sample at basically right angles with respect to the x-rays directed to the sample and at a basically right angle with respect to each other. This embodiment allows a very simple switching between an investigation of the bevel and the flat side of the wafer, with only requiring a minimum of moving parts, namely the handling stage.

Also within the scope of the present invention is the use of an inventive apparatus as described above, for detecting contaminations on the bevel of a wafer, in particular a silicon wafer, by means of XRF. The XRF analysis is non-destructive and can give immediate results on the contamination level. Note that typical contaminations looked for by means of the invention include Al (from grippers) and Na (from salt contained in human sweat),In a preferred variant of the inventive use, a gallium L line is used for x-ray generation in the x-ray source. This has shown good results in practice; gallium can well be used in a metal jet, since gallium has a relatively low melting point of about 30° C. and therefore needs only a minimum of heating.

Further within the scope of the present invention is a method for investigating the surface of the bevel of a wafer, in particular a Si wafer, wherein an x-ray beam is directed onto the bevel of the wafer and fluorescent x-rays emitted by the wafer are detected by EDS (EDS=energy dispersive spectroscopy). The spectra of contaminations will make them immediately observable.

Further advantages can be extracted from the description and the enclosed drawing. The features mentioned above and below can be used in accordance with the invention either individually or collectively in any combination. The embodiments mentioned are not to be understood as exhaustive enumeration but rather have exemplary character for the description of the invention.

The invention is shown in the drawing.

BRIEF DESCRIPTION OF THE DRAWING

FIG. 2a shows the apparatus of FIG. 1a, in a schematic side view, in a second operation mode wherein auxiliary x-ray optics are positioned to direct x-rays on the flat side of the wafer;

FIG. 2b shows the apparatus of FIG. 2a, in the second operation mode, in a schematic top view

DESCRIPTION OF THE PREFERRED EMBODIMENT

Figure 1A:
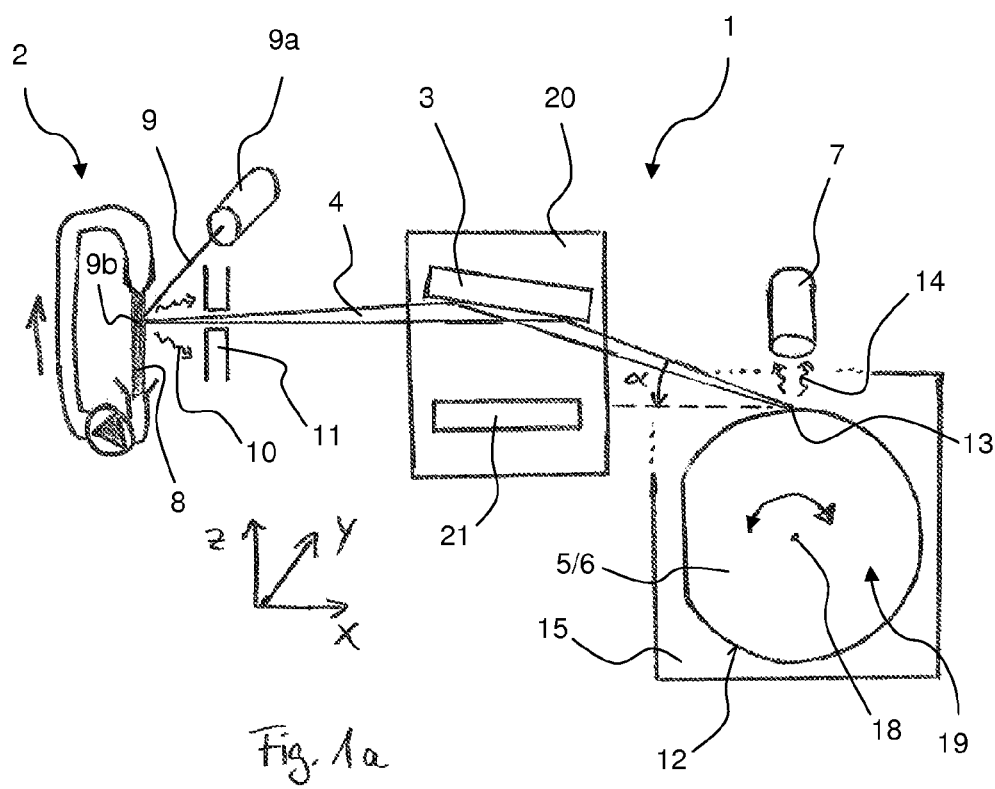
FIG. 1a shows an inventive XRF measurement apparatus, in a schematic side view, in a first operation mode wherein x-ray optics are positioned to direct x-rays on the bevel of a wafer.
Figure 1B:
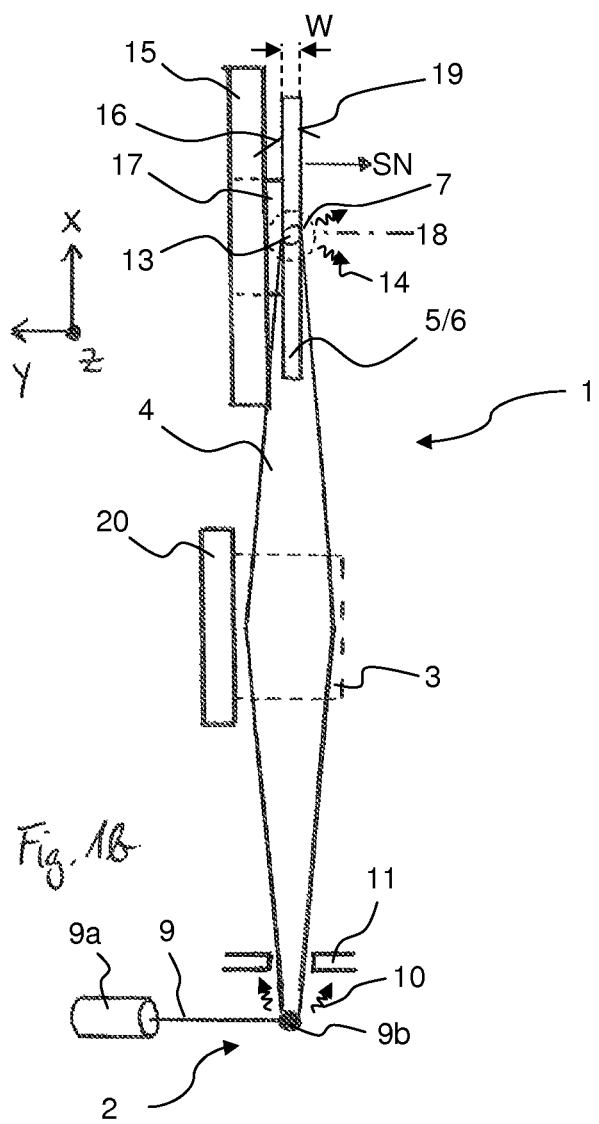
FIG. 1b shows the apparatus of FIG. 1a, in the first operation mode, in a schematic top view.

FIGS. 1a and 1b illustrate an embodiment of an inventive XRF measurement apparatus 1 by way of example, in a side view (FIG. 1a) and a top view (FIG. 1b).

The apparatus 1 comprises an x-ray source 2, x-ray optics 3 directing x-rays 4 from the x-ray source 2 to a sample 5, which is a disc shaped wafer 6, and an EDS detector 7.

The x-ray source 2 is, in the illustrated embodiment, of metal jet type, with a jet of liquid metal 8, for example slightly heated gallium, being hit by an electron beam 9 at a focal spot 9b. The electron beam 9 is generated by an electron beam source 9a; note that the electron beam 9 and metal jet 8 preferably propagate in vacuum. At the focal spot 9b of the electron beam 9, characteristic x-rays 10 and Bremsstrahlung are emitted. A fraction of the generated x-rays which passes an aperture 11 and is used as x-rays 4 (or primary beam) in the subsequent experimental setup. The brilliance of the x-ray source 2 together with the x-ray optics 3 is here at about $10^8$ counts/(sec mm$^2$).

The x-rays 4 are directed towards the sample 5 by means of x-ray optics 3, here a double curved multilayer mirror, mounted on a first stage 20. In the example shown, the x-rays 4 are focused in two dimensions onto the bevel 12 of the wafer 6 by means of the x-ray optics 3, with a matching (equal) width W of the x-rays 4 and the wafer at a focal spot 13. If desired, the x-ray optics 3 may be chosen such that the focal spot 13 is a 1:1 image of the focal spot 9b. The multilayer mirror also causes a monochromatization of the x-rays 4. The x-rays 4 hit the bevel 12 at an angle $\alpha$ with respect to the tangent of the bevel 12 of the wafer 6 at the focal spot 13; the tangent (see dashed line in FIG. 1a) represents the wafer surface at the focal spot 13 here. The angle $\alpha$ is typically between 0.05° and 6°, so total reflection occurs at the wafer surface (not shown in detail). Note that the figures exaggerate some angles and proportions in order to make them better visible. Further note that the angle $\alpha$ is here measured against the farther outer part of the x-ray beam; the beam size may be determined by the half maximum lines of the photon flux.

At the focal spot 13, fluorescent (characteristic) x-rays 14 are emitted, which may originate from the material of the wafer 6, and from contaminations on the surface of the wafer 6. By means of the EDS detector 7, the fluorescent x-rays 14 are detected in an energy resolved manner. The EDS detector 7 is located directly above the focal spot 13 in order to receive a maximum fraction of the fluorescent x-rays 14.

The wafer 6 is mounted on a second stage 15, which grabs the wafer 6 from its back side 16 by means of a vacuum gripper 17. The vacuum gripper 17 is rotatable with respect to a rotation axis 18 perpendicular to the flat side 19 of the wafer 6, in order to subsequently expose the complete bevel 12 to the x-rays 4.

In the embodiment shown, the x-rays 4 propagate in FIGS. 1a, 1b basically parallel to the vertical xz plane, and mostly horizontally in x; the tangent of the bevel 12 at the focal spot 13 runs horizontally (in x). The flat side 19 of the wafer 6 is oriented vertically, in parallel to the xz plane, too, with the surface normal SN of the flat side 19 and the rotation axis 18 running horizontally (in y direction).

The apparatus 1 can be switched from a first operation mode, which is illustrated in FIGS. 1a, 1b and has been explained above, to a second operation mode, which is illustrated in FIG. 2a (side view) and FIG. 2b (top view). In this second operation mode, the flat side 19 of the wafer 6 may be investigated by means of XRF. In FIGS. 2a and 2b, only the major differences to the setup of FIGS. 1a and 1b are explained in detail, and for simplification, the x-ray source 2 is not shown in detail.

For being able to switch between the operation modes, the first stage 20 is built as a first moving stage 20. By means of a motor (not shown), the first moving stage 20 can be moved in a vertical direction (z direction). In a lower position (see also FIG. 1a), x-ray optics 3 are in the path of the x-rays 4, whereas in an upper position (shown in FIG. 2a), auxiliary optics 21 are in the path of the x-rays 4. The auxiliary optics 21 comprise a double curved multilayer mirror again, which is oriented to deflect the x-rays 4 in the horizontal plane (yx-plane) and to focus the x-rays in two dimensions onto a focal spot 22 on the flat side 19 of the wafer 6. Note that the auxiliary x-ray optics 21 are placed on a wedge 23 to ensure a proper position, since the first moving stage 20 typically cannot be pivoted.

Further for switching between the operation modes, the second stage 15 for the wafer 6 is built as a second moving stage 15. By means of one or several motors (not shown), the second moving stage 15 can be moved in all translative directions x, y, z, and rotated with respect to a vertical axis 24. This allows the wafer 6 to be placed as shown in FIGS. 2a, 2b, and to scan the surface of the flat side 19 with the stationary focal spot 22. The x-rays 4 hit the flat side 19 at an angle $\beta$ of typically between 0.05° and 6°, again measured against the farther outer part (outer edge) of the incoming x-ray beam.

Further, in the embodiment shown, the EDS detector 7 can also be moved, preferably with a motorized stage (not shown), so the EDS detector 7 can be placed directly above the focal spot 22 in the second operation mode, too.

Figure 3A:
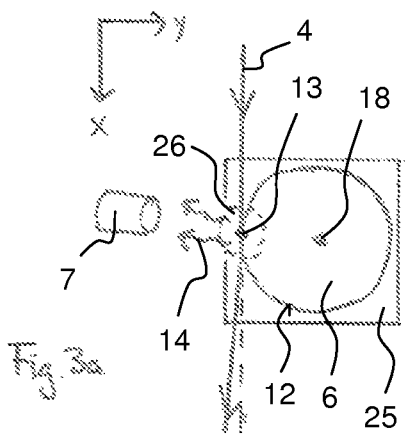
FIG. 3a shows a rear part of an inventive measurement apparatus, in a schematic top view, with a handling stage position allowing investigating the bevel of a wafer.
Figure 3C:
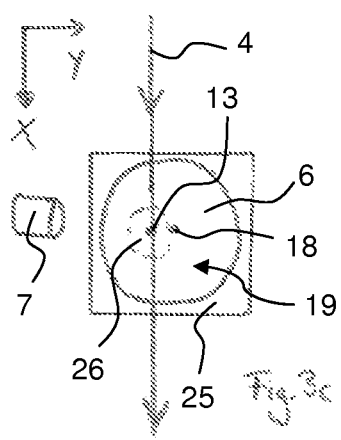
FIG. 3c shows the rear part of FIG. 3a, in a schematic top view, with a handling stage position allowing investigating the flat side of the wafer.
Figure 3B:
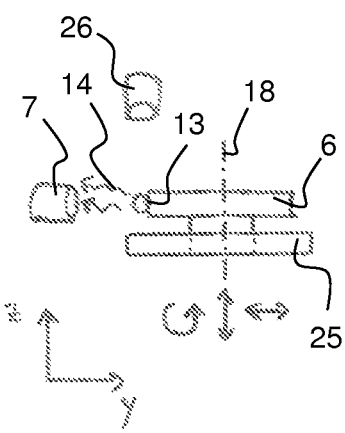
FIG. 3b shows the rear part of FIG. 3a, in a schematic side view.
Figure 3D:
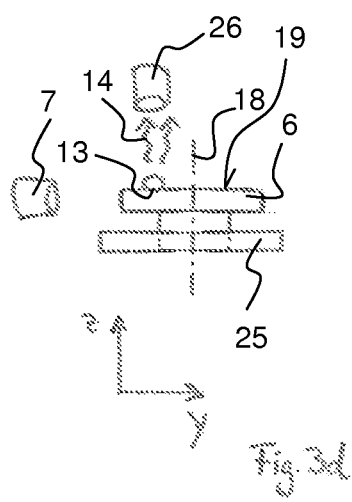
FIG. 3d shows the rear part of FIG. 3c, in a schematic side view.

FIGS. 3a through 3d illustrate another inventive apparatus, showing only the rear part (i.e. omitting the x-ray source and the x-ray optics, compare FIG. 1a, 1b for these components), which can be switched between a first operation mode in which the bevel of the wafer is investigated (see FIGS. 3a, 3b), and a second operation mode in which the flat side of the wafer is investigated (see FIGS. 3c, 3d).

In the first operation mode, compare FIGS. 3a (top view) and FIG. 3b (side view, perpendicular to the propagation direction of the x-rays 4), the x-rays 4 hit the bevel 12 of the wafer 6, compare focal spot 13. The x-rays 4 hit the bevel 12 at a small angle, such as about 1° against the tangent of the wafer 6 in the bevel region, so they are totally reflected. At the focal spot 13, characteristic x-rays 14 are emitted, which can be detected by an EDS detector 7. The EDS detector 7 is fixed at the height (sideways) of the wafer 6, receiving the characteristic x-rays 14 at a basically right angle with respect to the incoming x-rays 4, for XRF analysis.

The wafer 6 is held on a handling stage 25, which has been positioned at the correct height (z position) and traverse position (y position) such that the x-rays 4 hit the wafer 6 at the bevel 12 at said small angle, i.e. almost tangentially. During measurement, the wafer 6 is slowly rotated (typically in an incremented way) to check the complete circumference. Typically, the handling stage 25 is motorized for z and y position adjustments, and for rotation about the rotation axis 18.

Before or after measurement of the bevel, the flat side 19 of the wafer 6 may also be investigated by XRF with the apparatus, compare FIG. 3c (top view) and FIG. 3d (side view, in a direction perpendicular to the propagation direction of the x-rays 4), in a second operation mode. As compared to FIGS. 3a and 3b, the handling stage 25 has been moved slightly downward and to the left for this purpose. In this movement position, the x-rays 4 hit the wafer 6 at the flat side 19 under a small angle, such as 1°, against the plane of the flat side 19, and are totally reflected. In order to scan the flat side surface of the wafer 6 completely, the handling stage 25 is moved in an incremented way in y direction, and at each y position, the wafer 6 is rotated about rotational axis 18 over a full turn (typically in an incremented way). Characteristic x-rays 14 emitted at the focal spot 13 are detected with a further EDS detector 26, fixed above the wafer 6. The further EDS detector 26 is positioned to receive the characteristic x-rays 14 at a basically right angle with respect to the x-rays 4 again.

Note that the EDS detector 7 and the further EDS detector 26 are oriented at right angles with respect to their field of view, with only one of them operating at a time, depending on the operation mode. For switching between the modes here, it is not necessary to move or exchange the x-ray optics or the EDS detectors 7, 26, but only movement of the handling stage 25 or the wafer 6, respectively, is required.

I claim:

1. An XRF (XRF=x-ray fluorescence) measurement apparatus comprising:
   a sample, wherein said sample is a wafer or an Si wafer having a bevel;
   an x-ray source for generating x-rays;
   x-ray optics elements, said x-ray optics elements being disposed, structured and dimensioned to direct x-rays from the x-ray source onto said bevel of said wafer, wherein a combination of said x-ray source and said x-ray optics elements drive generated x-rays to a brilliance of at least $5*10^7$ counts/sec mm$^2$;
   an EDS (EDS=energy dispersive spectroscopy) detector for detecting fluorescent x-rays from said wafer;
   auxiliary x-ray optics elements for directing x-rays from said x-ray source onto said wafer; and
   a switching element for switching the apparatus between a first operation mode and a second operation mode, wherein, in said first operation mode, said x-ray optics elements are positioned to direct x-rays from said x-ray source onto said bevel of said wafer and, in said second operation mode, said auxiliary x-ray optics elements are positioned to direct x-rays from said x-ray source onto a flat side of said wafer, wherein said switching element comprises a first moving stage for exchanging said x-ray optics elements with said auxiliary x-ray optics elements by displacing said x-ray optics elements and said auxiliary x-ray optics elements substantially transverse to a direction of travel of the x-rays, said switching element also comprising a second moving stage for pivoting and shifting said wafer relative to a path of the x-rays when switching from said first to said second operation mode.

2. The apparatus of claim 1, wherein said brilliance is at least $1*10^8$ counts/sec mm$^2$.

3. The apparatus of claim 1, wherein said x-ray optics elements and said wafer are positioned such that the x-rays strike a surface of said bevel at an angle of between 0.05° and 6°.

4. The apparatus of claim 1, wherein said x-ray optics elements and said wafer are positioned such that the x-rays directed onto said wafer propagate substantially in an x-z plane parallel to a flat side of said wafer.

5. The apparatus of claim 1, wherein a surface normal of a flat side of said wafer is oriented horizontally.

6. The apparatus of claim 1, wherein the x-rays directed onto said wafer propagate in a substantially horizontal x-direction.

7. The apparatus of claim 1, wherein said x-ray source is of a metal jet target type.

8. The apparatus of claim 1, wherein said x-ray optics elements include a Montel mirror, a Goebel mirror or a double curved multilayer mirror.

9. The apparatus of claim 1, wherein said bevel of said wafer is located in a focus of said x-ray optics elements.

10. The apparatus of claim 1, wherein, at a position on a surface of said wafer, the x-rays directed onto said wafer have a width that matches a width of said wafer.

11. The apparatus of claim 1, the apparatus further comprising:
    a further EDS detector for detecting fluorescent x-rays from said wafer; and
    a handling stage for shifting said wafer relative to a path of the x-rays directed onto said wafer in two independent directions transverse to the x-rays directed onto the sample and for rotating said wafer with respect to a rotation axis perpendicular to a flat side of said wafer.

12. The apparatus of claim 11, wherein said two independent directions are mutually orthogonal directions.

13. The apparatus of claim 11, wherein said EDS detector and said further EDS detector view said wafer at substantially right angles with respect to the x-rays directed onto said wafer and at a substantially right angle with respect to each other.

14. A method for examining a wafer using the apparatus of claim 1, the method comprising the steps of:
    a) detecting fluorescent x-rays from the wafer; and
    b) determining contaminations on said bevel of said wafer or said silicon wafer by means of XRF.

15. The method of claim 14, wherein a gallium L line is utilized for x-ray generation in said x-ray source.

* * * * *